United States Patent [19]

Brame

[11] Patent Number: 4,490,613

[45] Date of Patent: Dec. 25, 1984

[54] INFRARED HYDROCARBON REMOTE SENSOR

[76] Inventor: Durward B. Brame, 2510 Richmond Dr., Arlington, Tex. 76014

[21] Appl. No.: 343,781

[22] Filed: Jan. 29, 1982

[51] Int. Cl.³ .......................... G01J 5/08; G01J 5/48
[52] U.S. Cl. .................................... 250/341; 250/253
[58] Field of Search ............. 250/341, 340, 301, 253; 356/318

[56] References Cited

U.S. PATENT DOCUMENTS

| | | | |
|---|---|---|---|
| 3,651,395 | 3/1972 | Owen et al. | 324/337 |
| 3,761,715 | 9/1973 | Menzies | 250/338 |
| 3,783,284 | 1/1974 | McCormack | 250/339 |
| 3,829,694 | 8/1974 | Goto | 250/339 |
| 3,977,760 | 8/1976 | Ullstig | 350/6.4 |
| 4,100,481 | 7/1978 | Gournay | 324/337 |
| 4,132,943 | 1/1979 | Gournay et al. | 324/335 |
| 4,394,573 | 7/1983 | Correa et al. | 250/253 |

Primary Examiner—Janice A. Howell
Assistant Examiner—Constantine Hannaher
Attorney, Agent, or Firm—Head, Johnson & Stevenson

[57] ABSTRACT

A method of locating potential oil and gas deposits by directing a beam of coherent high-intensity infrared radiation into the atmosphere above and adjacent the earth's surface, the wave length of the beam being selected such that it energizes selected hydrocarbon gas molecules, the beam being scanned in a raster pattern, detecting re-radiation generated by hydrocarbon molecules in the atmosphere which are energized by the infrared radiation, converting the detected re-radiated energy into electrical signals, and displaying on a raster scanned imaging tube a pictorial representation employing the electrical signals to indicate the presence of hydrocarbon molecules as an indication of the possibility of deposits of oil and gas in the earth below.

15 Claims, 7 Drawing Figures

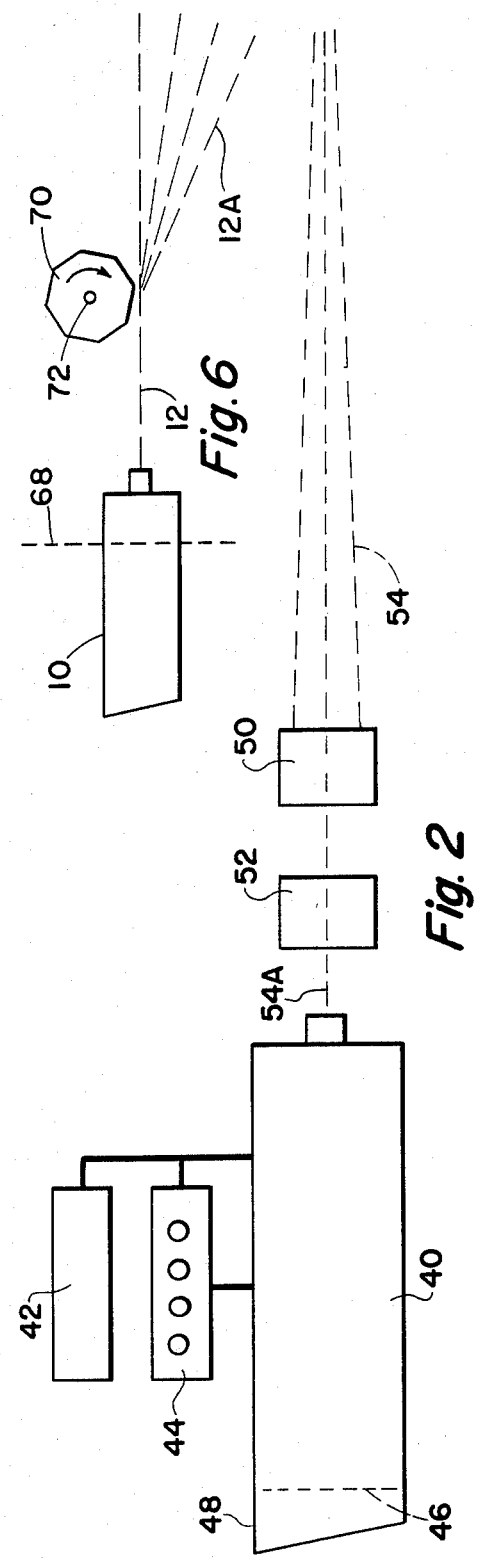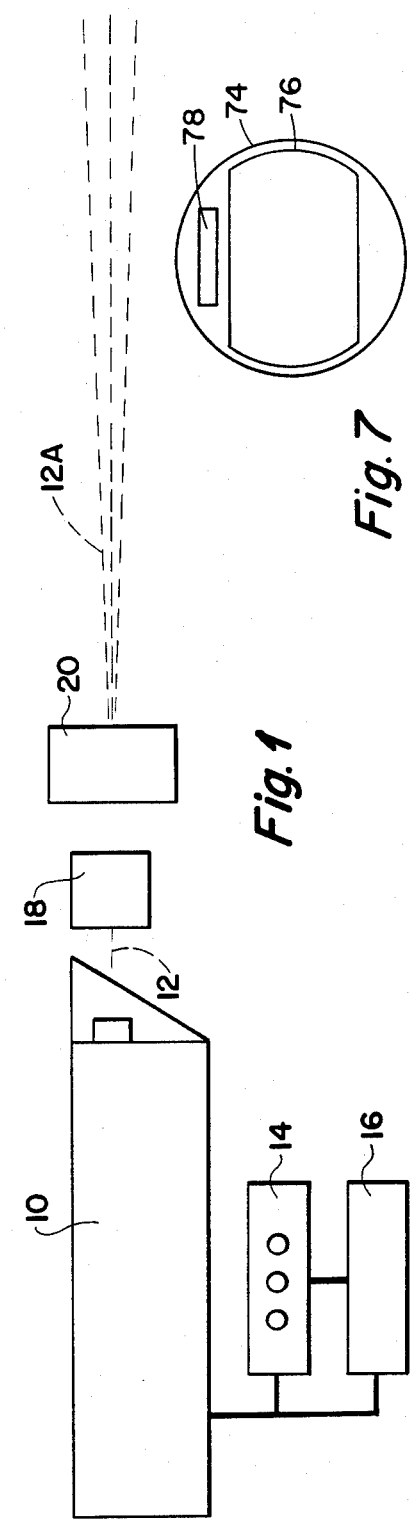

INFRARED HYDROCARBON REMOTE SENSOR

BACKGROUND AND PRIOR ART

A method is provided for giving an indication of the possible location of oil and gas deposits in the earth's surface. It is known that when oil and gas exist in subterranean formations molecules of such hydrocarbon products permeate upwardly in the earth's crust and eventually escape into the atmosphere. This seems to be true irrespective of the depth of the deposits, although obviously the shallower the deposits, the volume of the deposits, and the character of the overburden structure of the earth determines the amount of molecules which are dissipated into the atmosphere. The concept of detecting the possible presence of oil and gas deposits by detecting the presence of these molecules has been known in the past. One method of locating areas wherein the deposits occur is by collecting samples of gas from beneath the earth's surface. In this method probes are driven into the earth and gas samples withdrawn. By collecting samples in a grid pattern over a wide area, the presence of hydrocarbons, even in minute amounts, below the earth's surface can be detected and where concentrations of hydrocarbons exist there is indication that possible oil and gas deposits exist deeper in the earth's surface.

Others have utilized the concept of detecting the presence of hydrocarbon gases by energizing the molecules of gas in the atmosphere to cause them to re-radiate. The re-radiated energy is detected and utilized in various recording and display means. For background information as to this type of exploration method, see U.S. Pat. Nos. 3,651,395; 4,132,943; and 4,100,481. In addition, see co-pending application No. 275,105 filed June 18, 1981 entitled: "HYDROCARBON GAS REMOTE SENSING EXPLORATION SYSTEM" which is incorporated in this application by reference.

SUMMARY OF THE INVENTION

The present invention constitutes an improvement over the existing prior art by providing an improved means of detecting the presence of hydrocarbon gas molecules in the atmosphere. The method includes the step of directing a beam of coherent high-intensity infrared radiation into the atmosphere above and adjacent the earth's surface. The beam of coherent infrared radiation is transmitted in a preselected pattern such as in a raster scan or by the use of a revolving transmitter. Re-radiated energy generated by energized hydrocarbon molecules is detected and converted into electrical signals. These electrical signals are employed in a raster-scanned imaging tube to provide a visual indication and record of areas wherein hydrocarbon molecules are present in the atmosphere. Such pictorial indication and record may then be employed either alone or with other geophysical prospecting means in determining likely drilling sites for commercial production of oil or gas.

DESCRIPTION OF THE VIEWS OF THE DRAWINGS

FIG. 1 is a diagrammatic elevational view of apparatus for transmitting a high-intensity coherent beam of infrared radiation and for scanning the beam in a pattern, such as a raster pattern, to energize hydrocarbon molecules in the atmosphere.

FIG. 2 is a diagrammatic elevational view of apparatus to receive re-radiated energy from energized hydrocarbon molecules including an imaging system for displaying a pattern of the presence of energized hydrocarbon molecules in the atmosphere.

FIG. 6 is a diagrammatic elevational view of an apparatus for transmitting a high-intensity coherent beam of infrared radiation in which the beam is scanned vertically by use of a rotating polygon mirror. This arrangement is adaptable to transmitting through 360° by rotation of the entire apparatus about a vertical axis and is particularly useful for airborne surveying.

FIG. 7 depicts the face of an imaging tube as used in a receiver employed in the present method. A standard brightness patch is provided as a means of indicating the concentration of hydrocarbon molecules producing reradiated energy.

DETAILED DESCRIPTION

Figure 3:
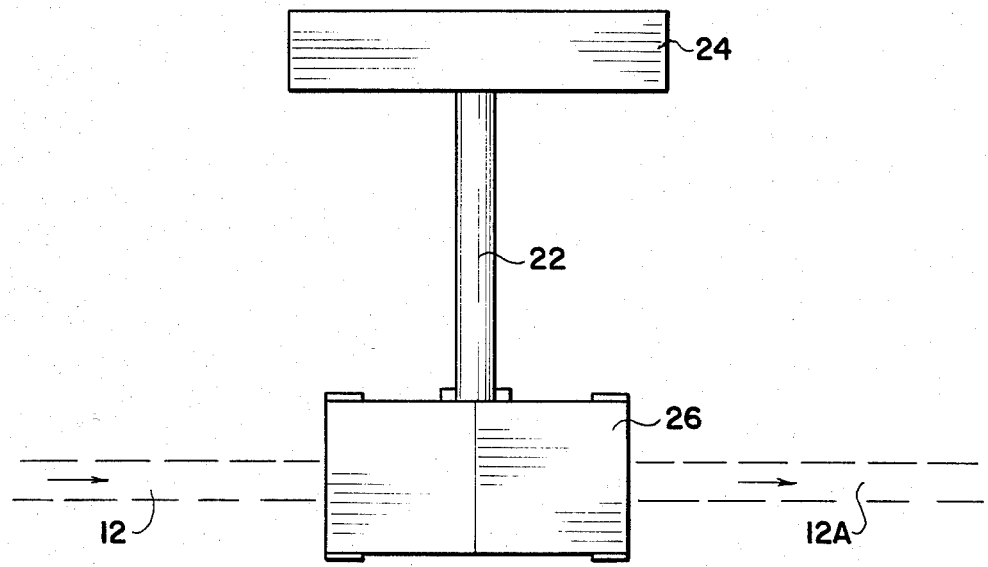
FIG. 3 is a plan view of a torsional bar activated scanning system for directing a pre-selected pattern of infrared transmission above and adjacent the earth's surface.

Referring to the drawings and first to FIG. 1, the elements employed in practicing the method of this invention are illustrated, and FIG. 1 particularly illustrates the portion employed for transmitting a high intensity coherent beam of infrared radiation which is employed to energize hydrocarbon molecules in the earth's atmosphere. A transmitter 10 provides a beam of coherent infrared energy 12. The transmitter 10 is preferably in the form of a laser. Many types of lasers are commercially available, including $CO_2$ lasers for providing the desired coherent beam. The transmitter 10 is preferably tuneable so that selectable frequencies of beam 12 may be employed for reasons which will be hereinafter set forth. The beam 10 may be either continuous or pulsed; however, for practical considerations, the pulsed beam is more advantageous. By pulsing beams of coherent light, a much higher intensity of the energy of the beam may be obtained for a transmitter of limited size.

A control panel 14 is employed to control transmitter 10. By means of control panel 14 the pulse rate of the laser which generates beam 12 may be regulated. The laser which is the basic element in the transmitter 10 is preferably, as previously indicated, tuneable so that coherent infrared beams of different frequencies may be selected, and the laser may be tuned directly in the transmitter 10 or by means of control panel 14, depending upon the details of construction of the equipment. A power supply 16 supplies the necessary electrical voltages to the transmitter 10 and control panel 14.

In order to map an area to determine the location of concentrations of hydrocarbon molecules in the atmosphere above the earth's surface, it is necessary that beam 12 be transmitted in a pattern. This could be accomplished by rotating the transmitter 12 through an arc while varying the angle of the transmitter relative to the horizontal. However, to rapidly move the transmitter 12 with all its beam generating and ancillary equipment would subject it to substantial stresses. It is therefore much more desirable that the transmitter 10 remain stationary during the mapping of a preselected area and that the beam 12 be deflected to cover a pattern which will produce useful information. The most desirable type pattern is that of a raster scan. This can be accomplished by means of a horizontal scanning unit 18 and a vertical scanning unit 20. The function of the horizontal scanning unit 18 is to sweep the beam 12 through a preselected horizontal angle which can be, such as 30°. The vertical scanning unit 20 functions to elevationally shift the beam, and usually this will be through a relatively small angle such as 5°. Therefore, by interrelating the scanning action of the horizontal and vertical scanning units 18 and 20, a raster pattern may be traced by the beam of coherent infrared energy, the beam after having been displaced being indicated by the numeral 12A.

Figure 4:
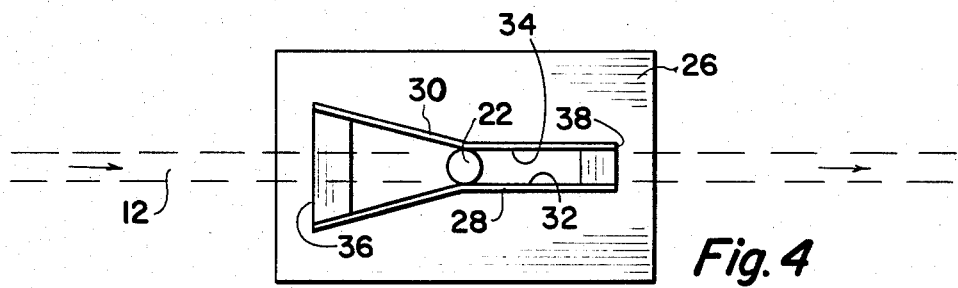
FIG. 4 is an elevational view of a mirror system which may be employed in scanning a beam of coherent infrared radiation as a part of the apparatus of FIG. 3.

While apparatus for reflecting the beam in the horizontal and vertical scanning units may take a variety of forms, exemplary apparatus is illustrated in FIGS. 3 and 4. Referring to FIG. 3, a torsional rod 22 is controlled by axial oscillator control 24. The control unit 24 is structurally supported in a manner not illustrated relative to the transmitter 10. Affixed at the outer end of torsional rod 22 is a scanning mirror system 26. The beam 12 from transmitter 10 enters the scanning mirror system 26; and as torsional rod 22 is oscillated about its axis, the beam 12A will be deflected in a plane perpendicular the axis of the torsional rod 22. Considering FIG. 3 as a plan view, that is, looking down on the apparatus, this would form a portion of the vertical scanning unit 20 of FIG. 1. When the scanning apparatus of FIG. 3 is employed for the horizontal scanning unit 18, the rod 22 is arranged so that its axis is vertical.

FIG. 4 shows diagrammatically a twin mirror system employed in the scanning mirror system 26. The structure 26 includes spaced apart mirror frames 28 and 30. The inside of mirror frame 28 has a mirror surface 32, and in like manner, the inside of frame 30 has a mirror surface 34. Beam 12 passes between the mirror surfaces 32 and 34. The mirror surfaces 32 and 34 are parallel to each other in both the vertical and horizontal planes. A beam 12 enters between the mirror surfaces 32 and 34 and is deflected as the scanning mirror system 26 is oscillated about the axis of torsional rod 22.

A scanning system of the type illustrated in FIGS. 3 and 4 may be utilized as the horizontal scanning unit 18 and a separate system of the same type utilized as the vertical scanning unit 20. In this way, the beam 12A may be scanned both vertically and horizontally to thereby project a raster pattern. In the typical raster pattern the number of horizontal traces is a small number compared to the number of vertical traces. That is, the vertical scanning unit 20 may scan vertically up to 200 times for each horizontal scan, thereby projecting at a given distance from the transmitter a rectangular target pattern for the beam 12A.

Referring now to FIG. 2, the detection system employed in the method of this invention is illustrated diagrammatically and consists of an imaging system display 40 supplied by a power supply 42 and operated by a control panel 44. As previously indicated the high intensity coherent infrared beam 12A, which is projected out in a pattern (preferably a raster scan pattern) over the surface of the earth, will energize hydrocarbon molecules in the atmosphere. These hydrocarbon molecules when reverting from their energized back to their normal state re-radiate energy at a somewhat different frequency than that of beam 12A. This re-radiated energy is dissipated in all directions, and a portion thereof is received back at the imaging system display 40. The imaging system display includes means for detecting the invisible infrared radiation which is re-radiated by hydrocarbon molecules, which means may be in the form of highly sensitive photovoltaic cells or a highly sensitive video camera designed to respond to infrared light. The detection system converts the signals received into electrical signals which are applied to apparatus, such as a cathode ray tube or other type of imaging tube, for converting the received signals into visual signals. The visual signals may be displayed on a screen 46 of a imaging tube which is protected from direct sunlight by shield 48.

In order to identify the type of hydrocarbon molecules which is re-radiating energy, it is important that the wave length of the re-radiated energy be accurately known. This can be accomplished by means of first passing the re-radiated energy through a neutral density filter unit 50 and then through an infrared filter turret 52. The re-radiated beam 54 after passing through the neutral density filter unit 50 and the infrared filter turret 52 provides a beam 54A of a preselected frequency band indicative of the energy re-radiated by certain hydrocarbon molecules such as methane, ethane, propane, or butane. Each of the different types of hydrocarbon molecules have distinct resonant frequencies. By properly selecting the frequency of transmission from the tuned laser producing beam 12 and the proper filter arrangement in filter turret 52, a specific wave length or window of wave lengths may be selected so that particular hydrocarbon molecules occurring in the earth's atmosphere may be identified. There are approximately 25 resonant frequencies for methane, 21 for ethane, 95 for propane, and 14 for butane. Some of these resonant frequencies are more predominant than others and therefore, it will be desirable to select one of these resonant frequencies which is most likely to be re-radiated when hydrocarbon molecules are bombarded by the infrared beam 12.

By means of the variable neutral density filter it is possible to regulate the returned re-radiated energy such that a numerical value can be placed on the brightness of this re-radiated energy which will in turn become a numerical value of the concentration of the hydrocarbon molecules present at or near the earth's surface. To assist in assigning a numerical value to the re-radiated energy received, a standard brightness patch may be employed as illustrated in FIG. 7. In FIG. 7 the face of the imaging tube is indicated by the numeral 74 with the area scanned indicated by the numeral 76. A standard brightness patch 78 may be established by placing an electron emitting material on the face of the imaging tube 74. Emitted electrons would be accelerated along with those electrons generated by the focused image on the face of the detector, and both would be displayed on the image. This would provide a brightness equal to the brightness of the standard. An operator could then read the numerical adjustment of the neutral density filter as a measurement of the concentration of hydrocarbon gases being scanned, to thereby derive a numerical rating for the molecule concentration.

The electrical signals generated as a result of the reception of re-radiated beam 54A can be displayed on the screen of a cathode ray tube wherein the display is coordinated with the raster scan of infrared beam 12. This can be accomplished by transmitting beam 12 in short bursts, receiving the re-radiated signal subsequent to the burst to produce an electrical signal displayed on screen 46, followed by a burst of energy from beam 12 and a continuous repetition of this arrangement. This can be carried out by the use of a pulsed laser. In this manner a picture can be drawn on cathode ray tube screen 46 pictorially displaying the area over which the infrared beam is directed and revealing the absence or presence of hydrocarbon molecules in the atmosphere. Where such molecules occur in density, the indication is that they are escaping at that point from the earth's surface, suggesting the possibility of hydrocarbon formations below the surface. By mapping large areas the spots most likely to produce commercial quantities of hydrocarbon gas or oil can be pinpointed.

The filters control the amount of return radiated energy which passes to the receiver. These filters can be so configured as to pass only a narrow band of infrared light and thereby to admit of reflected energy to form the image. This permits viewing the actual area scanned for landmarks, i.e., trees, hills, structures, fence posts, telephone posts, etc. and would be an aid for locating the anomaly precisely in relation to map features.

Figure 5:
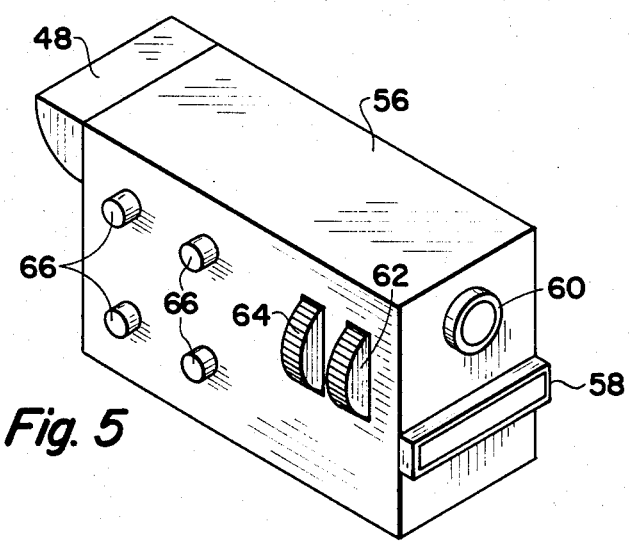
FIG. 5 is an isometric view of an exemplary apparatus which may be employed in practicing the invention for housing both the infrared coherent beam transmitter and apparatus for receiving re-radiated signals and for providing a pictorial indication of the presence of energized hydrocarbon molecules in the atmosphere.

In FIGS. 1 and 2 the transmitter 10 having the laser mechanism therein is indicated as one unit and the image system display 40 which receives the re-radiated signal is indicated as another unit. These units may be mounted together in one housing as indicated in FIG. 5. The housing 56 contains all of the elements indicated in FIGS. 1–4, and therefore constitutes a packaged infrared radiation hydrocarbon gas remote sensing system. The coherent high intensity infrared beam is transmitted through the aperture 58, the beam being swept in a raster pattern by the mechanism such as that illustrated in FIGS. 3 and 4 contained within the housing 56. The screen displaying the re-radiated signals is not shown but is supported in the rear of the housing 56 protected by the sun shield 48. The re-radiated signal passes through the aperture 60 and through a neutral density filter within housing 56, the filter being selectable by a neutral density filter control 62. The infrared filter turret employed to select the particlar infrared frequency used to provide electrical signals for the cathode ray tube is controlled by the filter turret control 64. The knobs 66 are indicative of control elements for selecting the frequency of transmission the pulse rate frequency, the brightness control for the cathode ray tube screen, etc. The integrated system such as contained in housing 56 may typically be mounted on a tripod (not shown) or supported on the bed of a truck or otherwise, so that the device may be moved from one location to another. The device permits rapid scanning of a selected area wherein the user can note the projection of location of hydrocarbon molecules in the atmosphere. By moving the device to a plurality of positions, the precise area of the earth over which the hydrocarbon molecules are concentrated can be established by triangulation.

While the system may be utilized by supporting the equipment on the earth or on a land vehicle, another method includes the application of the system to airborne surveying. While the equipment illustrated in FIGS. 1 through 5 may be employed for this purpose, the arrangement of FIG. 6 is particularly useful. Transmitter 10 is supported to an aircraft and is mounted for rotation about vertical axis 68. Supported as a part of the transmitter 10 is a polygon mirror 70 having a plurality of flat mirror surfaces on its periphery. The polygon mirror is rotated about a horizontal axis 72. The beam of coherent infrared energy 12 is deflected by the rotating mirror as indicated by 12A to rapidly scan a vertical pattern as the transmitter as a whole is rotated about vertical axis 68. The receiver, not shown in FIG. 6, may be affixed to the transmitter for simultaneous rotation with it or may be incorporated within the transmitter. By use of the system of FIG. 6, specially when mounted for airborne transportation, relatively large geographical areas may be surveyed in reduced time.

For information detailing the frequencies at which various hydrocarbon gases are energized and the frequencies at which hydrocarbon molecules re-radiate energy, see the National Bureau of Standards Publication NSRDS-NBS-39 entitled: "Tables of Molecular Vibrational Frequencies", Consolidated Volume I, which is incorporated herein by reference.

Utilizing the information taken from this publication, and after converting the molecular vibrational frequencies to wavelength it is possible to prepare a chart beginning with a wavelength of 3 micrometers and extending to a wavelength of 11 micrometers with each molecule of interest located on this chart by wavelength.

This exercise resulted in the very useful information that there exists regions in this spectrum (i.e. 3 micrometers to 11 micrometers) where the molecular vibrational frequencies of the molecules of interest are grouped together, thereby providing a "window" where these molecules can all be energized by a beam of infrared energy centered at the middle frequency of the window. The re-radiation of this entire window would be expected to return at a wavelength somewhat longer than the energizing wavelength.

For example, a window begins at 3.31+ micrometers and extends to 3.46+ micrometers and includes molecular vibrational frequencies of at least 26 separate molecules of methane, ethane, and propane.

The method of this invention is to energize this window at an infrared wavelength of around 3.4 micrometers. Re-radiation of these excited molecules could be expected at 3.5 to 3.6 micrometers. The exact radiating frequency (wavelength) and the re-radiated energy (wavelength) will best be determined by field testing.

A second window begins at 4.41+ micrometers and extends to 4.81+ micrometers. For this window radiation would be 4.6 micrometers and re-radiation would be expected at 4.8 micrometers. This window includes 24 molecules of methane, ethane, and propane.

A third window begins at 6.77+ micrometers and extends to 6.85+ micrometers. For this window radiation would be about 6.8 micrometers, and re-radiation would be expected at about 7.0 micrometers. This window includes 11 molecules of propane gas with only one of ethane, and no methane. This window would be useful for establishing that the anomaly includes the petroleum produced gases and not just methane (Marsh gas).

A next window begins at 7.18 micrometers and extends to 7.27 micrometers. Radiation would be set at 7.2 micrometers and re-radiation would be expected at about 7.4 micrometers. This window includes only propane gas.

Another window begins at 9.38 micrometers and extends to 9.414 micrometers. Radiation energy wavelength would be 9.4 micrometers, and re-radiation would be expected at about 9.6 micrometers. This window is also all propane gas.

The exact frequency used will depend somewhat upon the actual concentration of the various hydrocarbon molecules predominate in the geographical areas under investigation.

The above windows are those which appear to be the most useful since the vibrational frequencies of hydrocarbon molecules become very scattered beyond these frequency ranges.

While the invention has been described with a certain degree of particularity, it is manifest that many changes may be in the details of construction and the arrangement of the steps and components described herein without departing from the spirit and scope of this disclosure. It is understood that the invention is not limited to the embodiments set forth herein for exemplification, but is to be limited only by the scope of the attached claim or claims.

What is claimed:

1. A method of locating potential oil and gas deposits in the earth comprising:
    directing a beam of coherent high intensity infrared radiation into the atmosphere above and adjacent the earth's surface, the wave length of the beam being selected such that it energized selected hydrocarbon gas molecules;
    scanning the beam of infrared radiation in a preselected pattern; and
    detecting re-radiation generated by the energized hydrocarbon gas molecules.

2. The method of claim 1 in which said step of scanning the beam of radiation in a preselected pattern includes scanning the beam horizontally and vertically in the form of a raster configuration.

3. The method of claim 2 wherein the step of detecting re-radiation generated by energized hydrocarbon gas molecules includes converting the received energy into electrical signals and generating a display on a raster-scanned imaging tube by means of said electrical signals, the raster scan on the imaging tube corresponding to the raster scan configuration of the transmitted beam.

4. The method of claim 1, 2, or 3 in which the beam of coherent high intensity infrared radiation is continuously transmitted.

5. The method of claim 1, 2 or 3 in which the beam of coherent high intensity infrared radiation is intermittently transmitted.

6. The method of claim 1, 2 or 3 wherein the step of scanning said beam of infrared radiation includes passing said beam between spaced apart paralleled mirror surfaces and pivoting the mirror surfaces while maintaining parallelism to deflect said beam.

7. The method of claim 6 in which said mirror surfaces are vertical and are pivoted about vertical axii to sweep said beam horizontally.

8. The method of claim 6 in which said mirror surfaces are horizontal and are pivoted about horizontal axii to sweep said beam vertically.

9. The method of claim 1, 2 or 3 wherein the step of scanning said beam of infrared radiation includes passing said beam between spaced apart paralelled vertical mirror surfaces and spaced apart paralleled horizontal mirror surfaces, and pivoting said mirror surfaces while maintaining parallelism to deflect said beam horizontally and vertically in a raster pattern.

10. The method of claim 1, 2 or 3 including detecting reflected energy in addition to re-radiated energy to provide orientation information.

11. The method of claim 1 or 3 including directing the beam of coherent high intensity infrared radiation by apparatus rotated around a vertical axis while the beam is scanned vertically.

12. The method of claim 3 including passing received re-radiation energy through a variable neutral density filter before the received energy is converted to electrical signals to permit image brightness adjustment and quantitation.

13. The method of claim 3 including filtering received re-radiation energy by means of infrared filters before the received energy is converted to electrical signals to thereby convert only received energy of preselected frequency to electrical signals.

14. The method of claim 3 including first passing received re-radiation energy through a neutral density filter and then through at least one infrared filter to thereby convert only received energy in a preselected frequency range to electrical signals.

15. The method of claim 3 including generating a standard brightness display simultaneously with said step of generating a raster-scanned display.

* * * * *